(12) United States Patent
Dargazanli et al.

(10) Patent No.: US 7,619,089 B2
(45) Date of Patent: Nov. 17, 2009

(54) DERIVATIVES OF N-HETEROCYCLYLMETHYLBENZAMIDES, PREPARATION METHOD THEREOF AND APPLICATION OF SAME IN THERAPEUTICS

(75) Inventors: Gihad Dargazanli, Cachan (FR); Genevieve Estenne-Bouhtou, Chevilly-Larue (FR); Pascale Magat, Chilly Mazarin (FR); Benoit Marabout, Massy (FR); Pierre Roger, Montigny le Bretonneux (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 11/858,436

(22) Filed: Sep. 20, 2007

(65) Prior Publication Data

US 2008/0070941 A1    Mar. 20, 2008

Related U.S. Application Data

(60) Division of application No. 11/404,273, filed on Apr. 14, 2006, now Pat. No. 7,288,656, which is a continuation of application No. PCT/FR2004/002643, filed on Oct. 15, 2004.

(30) Foreign Application Priority Data

Oct. 17, 2003  (FR) ................................. 03 12165

(51) Int. Cl.
C07D 453/02  (2006.01)
A01N 43/90  (2006.01)
(52) U.S. Cl. ...................................... 546/133; 514/305
(58) Field of Classification Search ................. 514/305; 546/133
See application file for complete search history.

(56) References Cited

U.S. PATENT DOCUMENTS 7,288,656 B2 * 10/2007 Dargazanli et al. .......... 546/133

FOREIGN PATENT DOCUMENTS

WO    WO 99/45011    9/1999

OTHER PUBLICATIONS

Kinney et al. The Journal of Neuroscience, Aug. 20, 2003 o 23(20):7586-7591.*
Baur, et. al., Catalytic Asymmetric Protonation of Fluoro-Enolic Species: Access to Optically Active 2-Fluoro-1-Tetralone, Tetrahedron: Asymmetry vol. 14, (2003) pp. 2755-2761.
Brunner, H., et. al., Alpha-Amino Acid Derivatives by Enantioselective Decarboxylation, Eur. J. Org. Chem. (2003) pp. 2854-2862.
Brunner, H., et. al., Asymmetric Catalysis, 131[+] Naproxen Derivatives by Enantioselective Decarboxylation, European Journal of Chem. (2000) pp. 2119-2133.
Gallardo, M.A., et. al., Influence of Hypo-Osmolality on the Activity of Short-Chain Neutral Amino Acid Carriers in Trout (*Salmo trutta*) Red Blood Cells, J. Membrance Biol. vol. 155, (1997) pp. 113-119.
Caulfield, W. L., et. al., The First Potent and Selective Inhibitors of the Glycine Transporter Type 2, Journal of Medicinal Chemistry (2001, pp. 2679-2682, vol. 44, No. 17).

* cited by examiner

*Primary Examiner*—D. Margaret Seaman
*Assistant Examiner*—Nizal S Chandrakumar
(74) *Attorney, Agent, or Firm*—Balaram Gupta

(57) ABSTRACT

The invention relates to compositions comprising a compound having general formula (I):

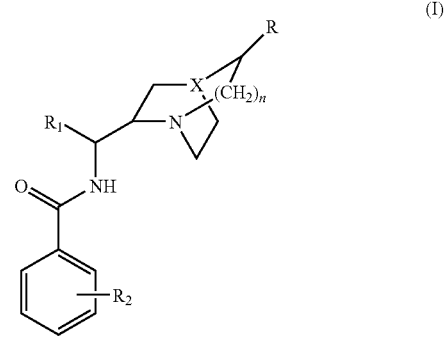

Wherein R, R1, R2, X and n are as described herein. Also disclosed and claimed in certain of the embodiments herein are the methods of preparation of compound of formula (I) and its use in therapeutics.

6 Claims, No Drawings

DERIVATIVES OF N-HETEROCYCLYLMETHYLBENZAMIDES, PREPARATION METHOD THEREOF AND APPLICATION OF SAME IN THERAPEUTICS

CROSS REFERENCE TO RELATED APPLICATIONS

This application is a division of U.S. application Ser. No. 11/404,273, filed Apr. 14, 2006, now allowed, which is a continuation of International application No. PCT/FR2004/002,643, filed Oct. 15, 2004, which is incorporated herein by reference in its entirety; which claims the benefit of priority of French Patent Application No. 03/12,165, filed Oct. 17, 2003.

BACKGROUND OF THE INVENTION

Field of the Invention

The subject of the present invention is N-heterocyclyl-methylbenzamide derivatives, their preparation and their therapeutic application.

SUMMARY OF THE INVENTION

The compounds of the invention correspond to general formula (I)

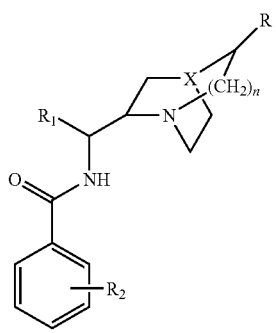

in which

R represents a hydrogen atom or a vinyl group;

n represents 0 or 1 or 2 when R represents a hydrogen atom and n represents 1 when R represents a vinyl group;

X represents a group of formula CH or a nitrogen atom when R represents a hydrogen atom and X represents a group of formula CH when R represents a vinyl group;

$R_1$ represents either a phenyl or naphthyl group optionally substituted with one or more substituents chosen from halogen atoms, linear or branched $(C_1\text{-}C_6)$alkyl, hydroxyl and $(C_1\text{-}C_6)$alkoxy groups, the trifluoromethyl group, or a cyclohexyl group, or a heteroaryl group chosen from the thienyl, pyridinyl, oxazolyl, furanyl, thiazolyl, quinolinyl, and isoquinolinyl groups;

$R_2$ represents either a hydrogen atom, or one or more substituents chosen from halogen atoms and the trifluoromethyl, $(C_1\text{-}C_6)$ alkyl, $(C_1\text{-}C_6)$ alkoxy, thienyl, phenyloxy, hydroxyl, mercapto, thio$(C_1\text{-}C_6)$alkyl and cyano groups or a group of general formula —$NR_4R_5$, $SO_2NR_4R_5$, —$SO_2$—$(C_1\text{-}C_6)$ alkyl, —$SO_2$-phenyl, —$CONR_4R_5$, —$COOR_7$, —CO—$(C_1\text{-}C_6)$alkyl, 'CO-phenyl, —NH-$COR_8$, —$NHSO_2$—$(C_1\text{-}C_6)$-alkyl, —$NHSO_2$-phenyl and —$NHSO_2NR_4R_5$ or a group of formula —$OCF_2O$ attached at the 2- and 3-positions of the phenyl group;

the groups $(C_1\text{-}C_6)$alkyl, $(C_1\text{-}C_6)$alkoxy, —$SO_2$—$(C_1\text{-}C_6)$ alkyl, —CO—$(C_1\text{-}C_6)$alkyl and —$NHSO_2$—$(C_1\text{-}C_6)$alkyl being optionally substituted with one or more groups $R_3$;

the groups phenyl, —$SO_2$-phenyl, —CO-phenyl and —$NHSO_2$-phenyl being optionally substituted with a group $R_6$;

$R_3$ represents a halogen atom, or a phenyl, $(C_1\text{-}C_6)$alkoxy or —$NR_4R_5$ group;

$R_4$ and $R_5$ represent, independently of each other, a hydrogen atom or a $(C_1\text{-}C_6)$alkyl group or $R_4$ and $R_5$ form with the nitrogen atom bearing them a pyrrolidine ring, a piperidine ring or a morpholine ring;

$R_6$ represents a hydrogen atom, a halogen atom, a trifluoromethyl group, a cyano group, a hydroxyl group, a mercapto group, a $(C_1\text{-}C_6)$alkyl or $(C_1\text{-}C_6)$alkoxy group;

$R_7$ represents a hydrogen atom or a $(C_1\text{-}C_6)$alkyl group optionally substituted with one or more groups $R_3$, or a phenyl group optionally substituted with a group $R_6$;

$R_8$ represents a $(C_1\text{-}C_6)$alkyl group optionally substituted with one or more groups $R_3$, or a $(C_1\text{-}C_6)$alkoxy group, or a phenyl group optionally substituted with a group $R_6$.

DETAILED DESCRIPTION OF THE INVENTION

Among the compounds of general formula (I), a number of subgroups of preferred compounds can be distinguished:

group 1: compounds of threo configuration and of general formula (I) in which n represents 0 or 1;

group 2: compounds of group 1 in whose formula X represents a group of formula CH;

group 3: compounds of group 2 in whose formula R represents a hydrogen atom;

group 4: compounds of group 3 in whose formula n represents 1;

group 5: compounds according to group 4 in whose formula $R_1$ represents an optionally substituted phenyl group.

The compounds of formula (I) may contain several asymmetric centers. They can therefore exist in the form of enantiomers or diastereoisomers. These enantiomers, diastereoisomers and mixtures thereof, including the racemic mixtures, form part of the invention.

More particularly, the compounds of formula (I), for which R═H, can exist in the form of threo ((1S,2S) and (1R,2R)) or erythro ((1S,2R) and (1R,2S)) diastereoisomers or of pure enantiomers or as a mixture of such isomers.

The compounds of formula (I) can exist in the form of bases or of addition salts with acids. Such addition salts form part of the invention.

These salts are advantageously prepared with pharmaceutically acceptable acids, but the salts of other acids useful, for example, for the purification or isolation of the compounds of formula (I) also form part of the invention. The compounds of formula (I) can also exist in the form of hydrates or solvates, namely in the form of associations or combinations with one or more molecules of water or with a solvent. Such hydrates and solvates also form part of the invention.

The compounds of the invention exhibit a particular activity as specific inhibitors of the glycine transporters glyt1 and/or glyt2.

The compounds of general formula (I) may be prepared by a method illustrated by scheme 1 which follows.

Scheme 1

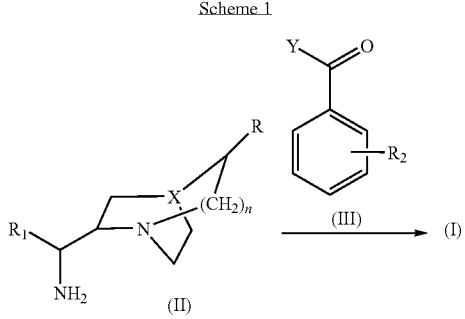

According to scheme 1, a diamine of general formula (II), in which n, X, R and $R_1$ are as defined above, is coupled with an activated acid or an acid chloride of general formula (III) in which Y represents a leaving group, such as a halogen atom, and $R_2$ is as defined above, using methods known to persons skilled in the art.

The diamines of general formula (II), in which R=H and n, X and $R_1$ are as defined above, may be prepared by a method illustrated by scheme 2 which follows.

Scheme 2

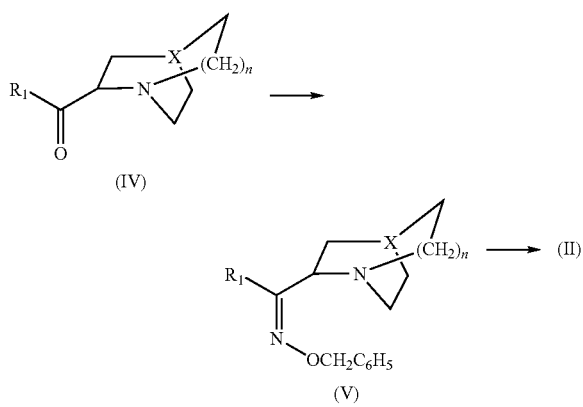

The ketone of general formula (IV), in which n, X and $R_1$ are as defined above, is reacted with benzyloxy-hydroxylamine hydrochloride, at the reflux temperature of pyridine, in order to obtain the oxime of general formula (V). The two forms Z and E of the oxime may be separated according to methods known to persons skilled in the art such as chromatography on a silica gel column.

The oxime (V), preferably in the Z hydrochloride form, is then reduced at the reflux temperature of tetrahydrofuran with lithium aluminum hydride to give the predominantly threo-diamine of general formula (II).

By reducing the E form of the oxime of general formula (V), a diamine (II) mixture is obtained in the form of the two diastereoisomers (threo/erythro).

The erythro- and threo-diastereoisomers may be separated according to methods known to persons skilled in the art such as chromatography on a silica gel column.

Another variant preparation of the diamines of general formula (II), in which R and $R_1$ are as defined above, n is equal to 1 and X is a CH, is illustrated by the scheme 3 which follows.

Scheme 3

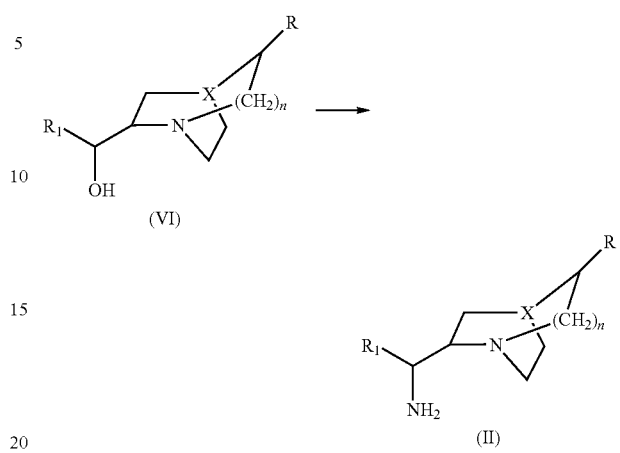

The alcohols of general formula (VI) are converted to amines by a Mitsunobu reaction according to the method described in *Bull. Soc. Chim. Belg.* (106), 1997, 77-84 and in *Tetrahedron: Asymmetry*, (6), 1995, 1699-1702, both of which are incorporated herein by reference in their entirety.

Moreover, the chiral compounds of general formula (I), corresponding to the enantiomers (1R,2R) or (1S,2S) of the threo-diastereoisomer and to the enantiomers (1S,2R) or (1R,2S) of the erythro-diastereoisomer, may also be obtained either by separating the racemic compounds by high performance liquid chromatography (HPLC) on a chiral column, or from the chiral amine obtained either by resolving the racemic amine of general formula (II), by the use of a chiral acid, such as tartaric acid, camphorsulfonic acid, dibenzoyl-tartaric acid, N-acetylleucine, by fractional and preferential recrystallization of a diastereoisomeric salt from a solvent of the alcohol type, or by enantioselective synthesis from an erythro- or threo-chiral alcohol using a method similar to that described in scheme 3. The chiral alcohols may be obtained by a method similar to that described in *Tetrahedron*, (55), 1999, 2795-2810, which is incorporated herein by reference in its entirety. In the case where R represents a vinyl group and $R_1$ represents a quinolinyl group, the diamine of general formula (II) may be prepared according to scheme 3 using the corresponding commercially available chiral alcohols.

The racemic ketone of general formula (IV) may be prepared either by deprotonation of an activated complex of the bridged cyclic amines and reaction with an electrophile, such as an ester or a Weinreb amide, according to a method similar to that described in *Chem. Commun.*, 1999, 1927-1928, which is incorporated herein by reference in its entirety, or by reaction of an organometallic compound on the ethyl ester of 2-quinuclidinic acid, according to a method similar to that described in *J. Med. Chem.*, 1980, 180-184, which is incorporated herein by reference in its entirety, or by oxidation of the corresponding alcohol obtained by various methods similar to those described in *J. Org. Chem.*, 50, 1985, 29-31 and *Chem. Comm.*, 1999, 1927-1929, which is incorporated herein by reference in its entirety, with oxidizing agents known to persons skilled in the art such as manganese dioxide or the oxalyl chloride-dimethyl sulfoxide system.

The alcohols of general formula (VI) may also be obtained by reducing the corresponding ketones of general formula (IV) under conditions known to persons skilled in the art.

The acids and acid chlorides of general formula (III) are commercially available or are prepared by analogy with methods known to persons skilled in the art.

For example, 4-amino-3-chloro-5-trifluoromethylbenzoic acid may be prepared by chlorination of 4-amino-5-trifluoromethylbenzoic acid with sulfuryl chloride in a chlorinated solvent such as chloroform, according to a method similar to that described in *Arzneim. Forsch.*, 34, 11a, (1984), 1668-1679, which is incorporated herein by reference in its entirety.

2,6-Dichloro-3-trifluoromethylbenzoic acid may be prepared by methods similar to those described in U.S. Pat. No. 3,823,134, which is incorporated herein by reference in its entirety.

The benzoic acids derived from sulfonamides may be prepared according to methods similar to those described in patents DE-2436263, BE-620741, DE-1158957, U.S. Pat. No. 3,112,337, GB-915259, U.S. Pat. No. 3,203,987, DE-642758, EP-68700,FR-2396757, DE-2734270, and in *J. Pharm. Pharmacol.* (1962), 14, 679-685. The meta-chlorosulfonylated acids may be obtained according to a method similar to those described in *J. Chem. Soc.* (C), (1968), 13, and in patents U.S. Pat. No. 2,273,444, DE-19929076, EP-0556674. All of the aforementioned references are incorporated herein by reference in their entirety.

Chlorosulfonylation at the ortho or para position may be carried out starting with a diazonium salt according to a method similar to that described in patent U.S. Pat. No. 3,663,615, which is incorporated herein by reference in its entirety, with 4-amino-3-chlorobenzoic acid.

The sulfonamides are obtained by the reaction of the chlorosulfonylated derivatives in the presence of an excess of amine in a solvent such as tetrahydrofuran, at room temperature or under reflux.

The secondary sulfonamides may be methylated according to a method similar to that described in patent BE-620741, which is incorporated herein by reference in its entirety. The primary sulfonamides may be reacted with an isocyanate, in a solvent such as tetrahydrofuran, in the presence of a base such as potassium carbonate. Some sulfoxide derivatives of benzoic acids are described in patents DE-2056912, DE-2901170 and U.S. Pat. No. 3,953,476 or may be obtained by methods similar to those described in patent BE-872585 and in *J. Org. Chem.* (1991), 56(1), 4976-4977. All of the aforementioned references are incorporated herein by reference in their entirety.

The benzoic acid derivatives of general formula (III), in which $R_2$ represents a branched alkyl group, may be prepared according to methods similar to that described in patent U.S. Pat. No. 4,879,426 and in *Syn. Lett.* (1996), 473-474 and *J. Med. Chem.* (2001), 44, 1085-1098. All of the aforementioned references are incorporated herein by reference in their entirety.

The benzoic acid derivatives of the biphenyl type may be prepared according to methods known to persons skilled in the art. Finally, the carbonylated benzoic acids may be synthesized according to methods similar to those described in patents U.S. Pat. No. 3,725,417 and GB-913100 and in *Chem. Pharm. Bull.*, (1988), 36(9), 3462-3467 and *J. Labelled Compd. Radiopharm.*, (1997), 39(6), 501-508. All of the aforementioned references are incorporated herein by reference in their entirety.

The esters or amides may be introduced by direct carbonylation with a strong base at the para position of the acid, under the conditions described in *Tetrahedron Lett.*, (2000), 41, 3157-3160, which is incorporated herein by reference in its entirety.

Finally, the cyano derivatives of benzoic acids are obtained by heating a halogenated benzoic acid or ester in the presence of potassium cyanide, a catalyst of the tetrakistriphenylphosphinepalladium type, in a solvent of the tetrahydrofuran type, according to a method similar to that described in J. Org. Chem. (1967) 62, 25, 8634-8639, which is incorporated herein by reference in its entirety.

Other acids and acid chlorides of general formula (III) may be obtained according to methods similar to those described in patents EP-0556672, U.S. Pat. No. 3,801,636 and in *J. Chem. Soc.*, (1927), 25, *Chem. Pharm. Bull.*, (1992), 1789-1792, *Aust. J. Chem.*, (1984), 1938-1950 and *J.O.C.*, 1980), 527. All of the aforementioned references are incorporated herein by reference in their entirety.

The examples which follow illustrate the preparation of a few compounds of the invention. It should be noted however that these examples are provided for illustration purposes and in no way limit the scope of the present invention. The elemental microanalyses, and the IR and NMR spectra, and the HPLC on a chiral column confirm the structures and the enantiomeric purities of the compounds obtained.

The numbers indicated in brackets in the headings of the examples correspond to those of the $1^{st}$ column of the table given later.

In the names of the compounds, the dash "-" forms part of the word, and the dash "_" only serves for splitting at the end of a line; it is deleted in the absence of splitting, and should not be replaced either by a normal dash or by a gap.

EXAMPLE 1

Compound No. 3 threo-2-Chloro-N-[(1-azabicyclo[2.2.2]oct-2-yl)phenyl-methyl]-3-trifluoromethylbenzamide hydrochloride 1:1

1.1.
(Z)-1-Azabicyclo[2.2.2]oct-2-yl(phenyl)methanone O-benzyloxime hydrochloride 2.2 g (9.35 mmol) of 1-azabicyclo[2.2.2]oct-2-yl(phenyl) methanone (*Chem. Commun.*, 1999, 1927-1928) and 3 g (18.69 mmol) of benzyloxyhydroxylamine hydrochloride in 50 ml of pyridine are introduced into a 100 ml round-bottomed flask equipped with magnetic stirring, and the mixture is heated under reflux for 20 h.

After evaporation of the solvents under reduced pressure, the residue is diluted with water and chloroform, the aqueous phase is separated, and it is extracted with chloroform. After washing the combined organic phases, drying over sodium sulfate and evaporation of the solvent under reduced pressure, the residue is purified by chromatography on a silica gel column, eluting with a mixture of chloroform and methanol.

There are obtained 0.5 g of a fraction corresponding to (E)-1-azabicyclo[2.2.2.]oct-2-yl(phenyl)methanone O-benzyloxime and 2.25 g of another fraction corresponding to (Z)-1-azabicyclo[2.2.2.]oct-2-yl(phenyl)methanone O-benzyloxime hydrochloride m.p. 195-197° C.

1.2. threo-[1-Azabicyclo[2.2.2.]oct-2-yl(phenyl)-methyl]amine 1.3 g (34.32 mmol) of lithium aluminum hydride in suspension in 10 ml of tetrahydrofuran are placed in a 250 ml three-necked flask equipped with magnetic stirring under a nitrogen atmosphere, 2.2 g (6.16 mmol) of (Z)-1-azabicyclo[2.2.2.]oct-2-yl(phenyl)methanone O-benzyloxime hydrochloride are added in portions and the mixture is heated under reflux for 2 h.

After cooling, the solution is hydrolyzed at 0° C. with successively 1.3 ml of water and then 1.3 ml of aqueous sodium hydroxide at 15% and 3.9 ml of water. The heterogeneous mixture is filtered on Celite®, the filtrate is concentrated under reduced pressure and then the residue is diluted with 1N hydrochloric acid and chloroform. The organic phase is separated and the aqueous phase is basified with aqueous ammonia. It is extracted twice with chloroform. After washing the combined organic phases, drying over sodium sulfate and evaporating the solvent under reduced pressure, 1.25 g of threo-[1-azabicyclo[2.2.2.]oct-2-yl(phenyl)methyl]-amine are obtained in the form of an oil which crystallizes and which is used as it is in the next step.

Melting point: 120-140° C.

1.3. threo-2-Chloro-N-[(1-azabicyclo[2.2.2]oct-2-yl)-phenylmethyl]-3-trifluoromethylbenzamide hydrochloride 1:1

0.51 g (2.12 mmol) of 2-chloro-3-trifluoromethylbenzoic acid chloride in solution in 5 ml of chloroform is placed in a 100 ml round-bottomed flask equipped with magnetic stirring, in the presence of 0.29 g (2.12 mmol) of potassium carbonate at 0° C., and a solution of 0.42 g (1.93 mmol) of threo-[1-azabicyclo-[2.2.2.]oct-2-yl(phenyl)methyl]amine in solution in 5 ml of chloroform is poured in and the mixture is stirred at room temperature for 6 h.

After hydrolyzing with water and diluting with chloroform, the aqueous phase is separated and it is extracted with chloroform. After washing the combined organic phases, drying over sodium sulfate and evaporating the solvent under reduced pressure, the residue is purified by chromatography on a silica gel column, eluting with a mixture of chloroform and methanol. 0.18 g of an oily product is obtained.

The latter is dissolved in a few ml of propan-2-ol, 6 ml of a 0.1N hydrochloric acid solution in propan-2-ol are added and the mixture is concentrated under reduced pressure in order to reduce the volume of the solvent. After trituration, 0.15 g of hydrochloride is finally isolated in the form of a solid.

Melting point: 257-262° C.

EXAMPLE 2

Compound No. 4 threo-2,6-Dichloro-N-[(1-azabicyclo[2.2.2]oct-2-yl)phenylmethyl]-3-trifluoromethylbenzamide hydrochloride 1:1

0.36 g (1.38 mmol) of 2,6-dichloro-3-trifluoromethyl-benzoic acid, 0.187 g (1.38 mmol) of hydroxybenzo-triazole, 0.264 g (1.38 mmol) of 1-[3-(dimethylamino)-propyl]-3-ethylcarbodiimide hydrochloride in solution in 7 ml of chloroform are introduced into a 100 ml round-bottomed flask equipped with magnetic stirring, and the mixture is stirred at room temperature for 30 min.

0.3 g (1.38 mmol) of threo-[1-azabicyclo[2.2.2.]oct-2 -yl (phenyl)methyl]amine in solution in 5 ml of chloroform is added and the mixture is stirred at room temperature overnight.

After hydrolyzing with water and diluting with chloroform, the aqueous phase is separated and it is extracted with chloroform. After washing the combined organic phases, drying over sodium sulfate and evaporating the solvent under reduced pressure, the residue is purified by chromatography on a silica gel column, eluting with a mixture of chloroform and methanol. 0.37 g of an oily product is obtained.

The latter is dissolved in a few ml of propan-2-ol, 20 ml of a 0.1N hydrochloric acid solution in propan-2-ol are added and the mixture is concentrated under reduced pressure in order to reduce the volume of the solvent. After trituration, 0.35 g of hydrochloride is finally isolated in the form of a solid.

Melting point: 270-273° C.

EXAMPLE 3

Compound No. 14

2-Chloro-N-(8α,9S)cinchonan-9-yl)-3-trifluoromethyl-benzamide hydrochloride 2:1

3.1. 8α-9S-Cinchonan-9-amine 0.74 g (2.5 mmol) of 8α,9R-cinchonan-9-ol (cinchonidine) and 0.79 g (3 mmol) of triphenyl-phosphine in suspension in 15 ml of tetrahydrofuran are introduced into a 100 ml three-necked flask equipped with magnetic stirring, under a nitrogen atmosphere, and 3.5 ml of a 0.9 M solution of hydrazoic acid in benzene (3 mmol) are added. A solution of 0.55 ml (2.75 mmol) of diisopropylcarbodiimide in 1.5 ml of tetrahydrofuran is added to this solution dropwise and the mixture is heated at 40° C. for 16 h.

0.65 g (2.5 mmol) of triphenylphosphine is added and the mixture is stirred for 30 min, 0.5 ml of water is added and the stirring is resumed for 6 h.

The mixture is hydrolyzed with 1N hydrochloric acid and diluted with chloroform. The aqueous phase is basified with aqueous ammonia and it is extracted several times with chloroform. After washing the combined organic phases, drying over sodium sulfate and evaporating the solvent under reduced pressure, 0.97 g of an orange-colored oil is obtained containing 8α,9S-cinchonan-9-amine which is used crude in the next step.

3.2. 2-Chloro-N-(8α,9S-cinchonan-9-yl)-3-trifluorometh-ylbenzamide hydrochloride 2:1

According to the method described in Example 1.3, starting with 0.97 g (3.3 mmol) of 8α,9S-cinchonan-9-amine, 0.84 g (3.4 mmol) of 2-chloro-3-trifluoromethyl-benzoic acid chloride and 0.5 g (3.63 mmol) of potassium carbonate, 0.360 g of oil is obtained which is dissolved in 30 ml of 1N hydrochloric acid. The aqueous phase is extracted with chloroform and then the solvent is evaporated under reduced pressure. 0.26 g of hydrochloride is thus obtained in the form of a white solid.

Melting point: 185-205° C.; $[\alpha]_D^{25}$=−5.4 (c=0.986, MeOH).

EXAMPLE 4

Compound No. 17

2,6-Dichloro-N-[(1S)-[(2S)(1-azabicyclo[2.2.2]oct-2-yl)phenylmethyl]-3-(trifluoromethyl)benzamide hydro-chloride 1:1

4.1 (1S)-[(2S)-1-Azabicyclo[2.2.2.]oct-2-yl(phenyl)-methyl]amine D-tartrate 9.4 g (43.45 mmol) of threo-[1-azabicyclo[2.2.2.]oct-2-yl (phenyl)methyl]amine are dissolved in 150 ml of ethanol. A solution of 6.52 g (43.45 mmol) of D-tartaric acid in solution in 200 ml of ethanol is poured in. After evaporating the solvent under reduced pressure, the residue is placed in 500 ml of a solution of ethanol and of water (9/1) and then heated until dissolution is obtained. After 3 successive recrystallizations, 5.39 g of (1S)-[(2S)-1-azabicyclo-[2.2.2.]oct-2-yl(phenyl)methyl]amine D-tartrate are obtained.

Melting point: 125-135° C. $[\alpha]_D^{25}$=−46.1 (c=0.616; MeOH).

4.2. 2,6-Dichloro-N-[(1S)-[(2S)(1-azabicyclo[2.2.2]oct-2-yl)phenylmethyl]-3-(trifluoromethyl)benzamide hydrochloride 1:1

3.33 g (12.02 mmol) of 2,6-dichloro-3-(trifluoro-methyl)benzoic acid chloride in solution in 30 ml of chloroform are placed in a 100 ml round-bottomed flask equipped with magnetic stirring in the presence of 1.82 g (13.22 mmol) of potassium carbonate at 0° C., and a solution of 2.6 g (12.02 mmol) of (1S)-[(2S)-1-azabicyclo[2.2.2.]oct-2-yl(phenyl)methyl]amine (obtained by basification of the salt described in 4.1, followed by extraction) in solution in 40 ml of chloroform is poured in and the mixture is stirred at room temperature for 6 h.

After hydrolyzing with water and diluting with chloroform, the aqueous phase is separated and it is extracted with chloroform. After washing the combined organic phases, drying over sodium sulfate and evaporating the solvent under reduced pressure, the residue is purified by chromatography on a silica gel column, eluting with a mixture of chloroform and methanol.

5.4 g of an oily product are obtained.

The latter is dissolved in a few ml of chloroform, 600 ml of a solution of ether saturated with hydrochloric acid are added, and the mixture is concentrated under reduced pressure. The residue is recrystallized from ethyl acetate. 4.7 g of 2,6-dichloro-N-[(1S)-[(2S)(1-azabicyclo[2.2.2]oct-2-yl)phenylmethyl]-3-(trifluoromethyl)benzamide hydrochloride are thus obtained.

Melting point: 264-268° C. $[\alpha]_D^{25}$=+61.1° (c=0.32; MeOH)

EXAMPLE 5

Compound No. 26 threo-N-[1-Azabicyclo[2.2.2]oct-2-yl(4-fluorophenyl)-methyl]-2,6-dichloro-3-(trifluoromethyl)benzamide hydrochloride 1:1

5.1 1-Azabicyclo[2.2.2]oct-2-yl(4-fluorophenyl)-methanol 1.11 g (10 mmol) of quinuclidine in 40 ml of dry tetrahydrofuran at 0° C. are placed in a 100 ml three-necked flask under argon. 1.33 ml (10.5 mmol) of ether-boron trifluoride complex are added dropwise and the mixture is stirred for 30 min at 0° C. (solution A). In parallel, 2.47 g (22 mmol) of dry potassium tert-butoxide in 60 ml of dry tetrahydrofuran are placed in a 250 ml three-necked flask under argon. The mixture is cooled to −70° C. and 22 ml of a 1M solution of sec-butyllithium in the cyclohexane/hexane mixture (22 mmol) are poured in dropwise while the temperature is kept below −60° C. (solution B). At the end of the addition, the solution A is delivered by a cannula-like tube into the solution B while the temperature is kept at around −70° C. The mixture is kept stirring for 2 h.

2.36 mol (22 mmol) of distilled 4-fluorobenzaldehyde in solution in 20 ml of tetrahydrofuran at −70° C. are placed in a 50 ml three-necked flask under argon. The solution B is delivered by a cannula-like tube while the temperature is kept at around −70° C. The resulting solution is left for 30 min at −70° C. and allowed to rise to −20° C. The mixture is then hydrolyzed with a 10% hydrochloric acid solution. The mixture is extracted with ether and then the aqueous phase is taken up and basified with aqueous ammonia. The mixture is extracted with chloroform and then the solvent is evaporated under reduced pressure. The residue is purified by flash chromatography on a silica gel column, eluting with a mixture of chloroform and methanol. 0.53 g of 1-azabicyclo[2.2.2]oct-2-yl(4-fluorophenyl)methanol is thus obtained in the form of a yellowish solid.

Melting point: 69-70° C.

5.2 1-Azabicyclo[2.2.2]oct-2-yl(4-fluorophenyl) meth-anone 1.3 ml of dimethyl sulfoxide in 40 ml of tetrahydrofuran at −70° C. are placed in a 250 ml three-necked flask under nitrogen, and 0.9 ml of oxalyl chloride (11 mmol) is added dropwise and the mixture is kept stirring for 30 min at this temperature. A solution of 1 g (4.6 mmol) of 1-azabicyclo[2.2.2]oct-2-yl(4-fluorophenyl)methanol in 40 ml of tetrahydrofuran is added dropwise. After 30 min, 4 ml (27.6 mmol) of triethylamine are added at −70° C. The reaction mixture is then stirred for 30 min at −70° C., for 30 min at 0° C. and then for 1 h at room temperature.

The mixture is poured into an aqueous ammonia solution and then extracted several times with chloroform. The organic phases are dried over sodium sulfate and evaporated under reduced pressure. The residue is purified by chromatography on a silica gel column, eluting with a mixture of chloroform and methanol. 1 g of 1-azabicyclo[2.2.2]oct-2-yl (4-fluorophenyl)methanone is thus obtained.

Melting point: 68-69° C.

5.3 (Z)-1-Azabicyclo[2.2.2]octyl(4-fluorophenyl) meth-anone O-benzyloxime hydrochloride According to the procedure described in Example 1.1, starting with 1.17 g (5 mmol) of ketone, 1.4 g of (Z)-1-azabicyclo[2.2.2]octyl(4-fluorophenyl)methanone O-benzyloxime hydrochloride are obtained after trituration, in ether, of the residue obtained after the treatment of the reaction.

Melting point: 202-203° C.

5.4 threo-1-Azabicyclo[2.2.2]octyl(4-fluorophenyl)-methanamine

According to the procedure described in 1.2, starting with 1.47 g (4.54 mmol) of (Z)-1-azabicyclo[2.2.2]oct-yl(4-fluorophenyl)methanone O-benzyloxime hydro-chloride, 1 g of threo-1-azabicyclo[2.2.2]octyl(4-fluorophenyl)methanamine (diastereoisomeric excess, de=90%).

5.5 N-[(S)-(2S)-1-Azabicyclo[2.2.2]oct-2-yl(4-fluoro-phenyl)methyl]-2,6-dichloro-3-(trifluoromethyl)benzamide hydrochloride 1:1

According to the procedure described in 1.3, starting with 0.39 g (1.66 mmol) of threo-1-azabicyclo-[2.2.2]octyl(4-fluorophenyl)methanamine, 0.5 g (1.83 mmol) of 2,6-dichloro-3-trifluoromethylbenzoic acid chloride, 0.25 g (1.83 mmol) of potassium carbonate, 0.79 g of threo-N-[1-azabicyclo[2.2.2]oct-2-yl(4-fluorophenyl)methyl]-2,6-dichloro-3-(trifluoro-methyl)benzamide is obtained, after purification by chromatography, in the form of an oil which is salified with a solution of gaseous hydrochloric acid in ethyl ether.

Melting point: 290-291° C.

The other compounds are obtained according to the methods described in Examples 1, 2 and 5 from other functionalized aldehydes.

The following Table 1 illustrates the chemical structures of a few compounds of the invention.

In the "R" column, —CH=CH$_2$ denotes a vinyl group, in the "R$_1$" column, C$_6$H$_5$ denotes a phenyl group and 4-C$_9$H$_6$N denotes a quinolin-4-yl group. In the "Salt" column, — denotes a compound in the base state, "HCl" denotes a hydrochloride and "tfa" denotes a trifluoroacetate.

The compounds 14, 19 to 23, 24 of the table exist in the hydrochloride or dihydrochloride form (see table) solvated with one or more water molecules.

The compounds 15 and 16 of the table form a pair of enantiomers which are separated by preparative HPLC using a 20 μm CHIRACEL® AD column and, as solvent, a 95/5 isohexane/propan-2-ol mixture, likewise for the compounds 17 and 18.

Table 2 gives the physical properties, the melting points and optical rotations of the compounds of the table. "(d)" indicates a melting point with decomposition.

TABLE 1

(I)

| No. | R$_1$ | R | X | n | R$_2$ | Salt | Stereochemistry |
|---|---|---|---|---|---|---|---|
| 1 | C$_6$H$_5$ | H | CH | 1 | 3-SO$_2$N(CH$_3$)$_2$, 4-Cl | — | threo (1R, 2R; 1S, 2S) |
| 2 | C$_6$H$_5$ | H | CH | 1 | 2-Cl, 5-CF$_3$ | HCl | threo (1R, 2R;.1S, 2S) |
| 3 | C$_6$H$_5$ | H | CH | 1 | 2-Cl, 3-CF$_3$ | HCl | threo (1R, 2R; 1S, 2S) |
| 4 | C$_6$H$_5$ | H | CH | 1 | 2,6-(Cl)$_2$, 3-CF$_3$ | HCl | threo (1R, 2R; 1S, 2S) |
| 5 | C$_6$H$_5$ | H | CH | 1 | 2-Cl, 3-CH$_3$, 6-F | HCl | threo (1R, 2R; 1S, 2S) |
| 6 | C$_6$H$_5$ | H | CH | 1 | 2-Cl, 3-CH$_3$ | HCl | threo (1R, 2R; 1S, 2S) |
| 7 | C$_6$H$_5$ | H | CH | 1 | 2,4,6-(Cl)$_3$ | HCl | threo (1R, 2R; 1S, 2S) |
| 8 | C$_6$H$_5$ | H | CH | 1 | 2-CH$_3$, 3-CF$_3$ | HCl | threo (1R, 2R; 1S, 2S) |
| 9 | C$_6$H$_5$ | H | CH | 1 | 2,6-(Cl)$_2$ | HCl | threo (1R, 2R; 1S, 2S) |
| 10 | C$_6$H$_5$ | H | CH | 1 | 2,5-(CF$_3$)$_2$ | HCl | threo (1R, 2R; 1S, 2S) |
| 11 | C$_6$H$_5$ | H | CH | 1 | 2-F, 3-Cl, 6-CF$_3$ | HCl | threo (1R, 2R; 1S, 2S) |
| 12 | C$_6$H$_5$ | H | CH | 1 | 2-CH$_3$, 3-Cl | HCl | threo (1R, 2R; 1S, 2S) |
| 13 | C$_6$H$_5$ | H | CH | 1 | 2,3-(Cl)$_2$ | HCl | threo (1R, 2R; 1S, 2S) |
| 14 | 4-C$_9$H$_6$N | CH=CH$_2$ | CH | 1 | 2-Cl, 3-CF$_3$ | 2HCl | (1S, 2S) |
| 15 | C$_6$H$_5$ | H | CH | 1 | 2-Cl, 3-CF$_3$ | tfa | (1R, 2R) |
| 16 | C$_6$H$_5$ | H | CH | 1 | 2-Cl, 3-CF$_3$ | tfa | (1S, 2S) |
| 17 | C$_6$H$_5$ | H | CH | 1 | 2,6-(Cl)$_2$, 3-CF$_3$ | HCl | (1S, 2S) |
| 18 | C$_6$H$_5$ | H | CH | 1 | 2,6-(Cl)$_3$, 3-CF$_3$ | HCl | (1R, 2R) |
| 19 | C$_6$H$_5$ | H | N | 1 | 2-Cl, 3-CF$_3$ | 2HCl | threo (1R, 2R; 1S, 2S) |
| 20 | C$_6$H$_5$ | H | N | 1 | 2,6-(Cl)$_2$, 3-CF$_3$ | 2HCl | threo (1R, 2R; 1S, 2S) |
| 21 | C$_6$H$_5$ | H | N | 1 | 2,6-(Cl)$_2$ | 2HCl | threo (1R, 2R; 1S, 2S) |
| 22 | C$_6$H$_5$ | H | N | 1 | 2-CH$_3$, 3-CF$_3$ | 2HCl | threo (1R, 2R; 1S, 2S) |
| 23 | C$_6$H$_5$ | H | N | 1 | 2-CH$_3$, 3-Cl | 2HCl | threo (1R, 2R; 1S, 2S) |
| 24 | C$_6$H$_5$ | H | CH | 1 | 3,5 (Cl)$_2$, 4-NH$_2$ | HCl | threo (1R, 2R; 1S, 2S) |
| 25 | 4-F-C$_6$H$_4$ | H | CH | 1 | 2-Cl, 3-CF$_3$ | HCl | threo (1R, 2R; 1S, 2S) |
| 26 | 4-F-C$_6$H$_4$ | H | CH | 1 | 2,6-(Cl)$_2$, 3-CF$_3$ | HCl | threo (1R, 2R; 1S, 2S) |
| 27 | 1-nephthyl | H | CH | 1 | 2,6-(Cl)$_2$, 3-CF$_3$ | HCl | threo (1R, 2R; 1S, 2S) |
| 28 | 1-naphthyl | H | CH | 1 | 2-Cl, 3-CF$_3$ | HCl | threo (1R, 2R; 1S, 2S) |
| 29 | 1-naphthyl | H | CH | 1 | 2-CH$_3$, 3-Cl | HCl | threo (1R, 2R; 1S, 2S) |
| 30 | 2-CH$_3$—C$_6$H$_4$ | H | CH | 1 | 2-Cl, 3-CF$_3$ | HCl | threo (1R, 2R; 1S, 2S) |
| 31 | 2-CH$_3$—C$_6$H$_4$ | H | CH | 1 | 2,6-(Cl)$_2$, 3-CF$_3$ | HCl | threo (1R, 2R; 1S, 2S) |
| 32 | C$_6$H$_5$ | H | CH | 1 | 6-CH$_3$, 3-Cl, 2-NH$_2$ | HCl | threo (1R, 2R; 1S, 2S) |
| 33 | C$_6$H$_5$ | H | CH | 1 | 3,6-(Cl)$_2$, 2-NH$_2$ | HCl | threo (1R, 2R; 1S, 2S) |
| 34 | C$_6$H$_5$ | H | CH | 1 | 2,6-(Cl)$_2$, 3-CH$_3$ | HCl | threo (1R, 2R; 1S, 2S) |
| 35 | C$_6$H$_5$ | H | CH | 1 | 2-CH$_3$, 3-Cl | HCl | (1S, 2S) |
| 36 | C$_6$H$_5$ | H | CH | 1 | 2-Cl, 3-CF$_3$ | HCl | erythro (1S, 2R; 1R, 2S) |
| 37 | 4-F—C$_6$H$_4$ | H | CH | 1 | 2-CH$_3$, 3-Cl | HCl | threo/erythro: 9/1 |
| 38 | 3-F—C$_6$H$_4$ | H | CH | 1 | 2,6-(Cl)$_2$, 3-CF$_3$ | HCl | threo (1R, 2R; 1S, 2S) |
| 39 | 3-F—C$_6$H$_4$ | H | CH | 1 | 2,6-(Cl)$_2$, 3-CF$_3$ | HCl | erythro (1S, 2R; 1R, 2S) |
| 40 | 4-F, 3-CH$_3$—C$_6$H$_3$ | H | CH | 1 | 2-CH$_3$, 3-OCH$_3$ | HCl | threo/erythro 1/1 |
| 41 | 4-F, 3-CH$_3$—C$_6$H$_3$ | H | CH | 1 | 3,5-(OCH$_3$)$_2$ | HCl | threo/erythro 1/1 |
| 42 | 4-F, 3-CH$_3$—C$_6$H$_3$ | H | CH | 1 | 2,6-(Cl)$_2$, 3-CF$_3$ | HCl | threo (1R, 2R; 1S, 2S) |

TABLE 1-continued

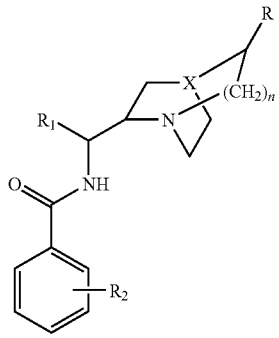

(I)

| No. | R₁ | R | X | n | R₂ | Salt | Stereochemistry |
|---|---|---|---|---|---|---|---|
| 43 | 3-F-C₆H₄ | H | CH | 1 | 2-CH₃, 3-OCH₃ | HCl | threo (1R, 2R; 1S, 2S) |
| 44 | C₆H₅ | H | CH | 1 | 2-OCH₃, 5-Cl | HCl | (1S, 2S) |
| 45 | C₆H₅ | H | CH | 1 | 2-Br, 5-OCH₃ | HCl | (1S, 2S) |
| 46 | C₆H₅ | H | CH | 1 | 2,3-(OCF₂O) | HCl | (1S, 2S) |
| 47 | C₆H₅ | H | CH | 1 | 2,6-(OCH₃)₂ | HCl | (1S, 2S) |
| 48 | C₆H₅ | H | CH | 1 | 3,5-(OCH₃)₂ | HCl | (1S, 2S) |
| 49 | C₆H₅ | H | CH | 1 | 2,3-(OCH₃)₂ | HCl | (1S, 2S) |
| 50 | C₆H₅ | H | CH | 1 | 2-NH₂, 3-CH₃ | 2HCl | (1S, 2S) |
| 51 | C₆H₅ | H | CH | 1 | 2-OCH₃, 3,6-(Cl)₂ | HCl | (1S, 2S) |
| 52 | C₆H₅ | H | CH | 1 | 3-(O—C₆H₅) | HCl | (1S, 2S) |
| 53 | C₆H₅ | H | CH | 1 | 2,5-(OCH₃)₂ | HCl | (1S, 2S) |
| 54 | C₆H₅ | H | CH | 1 | 2-CH₃, 3-OCH₃ | HCl | (1S, 2S) |
| 55 | C₆H₅ | H | CH | 1 | 2-OCH₃, 3,5(Cl)₂ | HCl | (1S, 2S) |
| 56 | C₆H₅ | H | CH | 1 | 2-Cl, 6-CH₃ | HCl | (1S, 2S) |
| 57 | C₆H₅ | H | CH | 1 | 2-NH₂, 6-CH₃ | 2HCl | (1S, 2S) |
| 58 | C₆H₅ | H | CH | 1 | 2-NH₂, 5-Br | 2HCl | (1S, 2S) |
| 59 | C₆H₅ | H | CH | 1 | 2-NH₂, 5-CH₃ | 2HCl | (1S, 2S) |
| 60 | C₆H₅ | H | CH | 1 | 2-OCH₃, 3-CH₃ | HCl | (1S, 2S) |
| 61 | C₆H₅ | H | CH | 1 | 2-NH₂, 5-OCH₃ | 2HCl | (1S, 2S) |
| 62 | C₆H₅ | H | CH | 1 | 2-NH₂, 3-OCH₃ | 2HCl | (1S, 2S) |
| 63 | C₆H₅ | H | CH | 1 | 2-Cl, 5-CH₃ | HCl | (1S, 2S) |
| 64 | C₆H₅ | H | CH | 1 | 2-OCH₃, 5-CH₃ | HCl | (1S, 2S) |
| 65 | C₆H₅ | H | CH | 1 | 2-CH₃, 3-OH | HCl | (1S, 2S) |
| 66 | C₆H₅ | H | CH | 1 | 2-CH₃, 5-Cl | HCl | (1S, 2S) |
| 67 | 4-OCH₃—C₆H₄ | H | CH | 1 | 2,6-(Cl)₂, 3-CF₃ | HCl | threo (1R, 2R; 1S, 2S) |
| 68 | 4-OH—C₆H₄ | H | CH | 1 | 2,6-(Cl)₂, 3-CF₃ | — | threo (1R, 2R; 1S, 2S) |
| 69 | 3-F—C₆H₄ | H | CH | 1 | 2-CH₃, 3-Cl | HCl | threo (1R, 2R; 1S, 2S) |

TABLE 2

| No. | m.p. (° C.) | [α]$_D^{25}$ (°) |
|---|---|---|
| 1 | 233-235 | — |
| 2 | 267-269 | — |
| 3 | 257-262 | — |
| 4 | 270-273 | — |
| 5 | 315-316 | — |
| 6 | 319-320 | — |
| 7 | >300 | — |
| 8 | 281-283 | — |
| 9 | 359-361 | — |
| 10 | 281-283 | — |
| 11 | 347-349 | — |
| 12 | 311-313 | — |
| 13 | 316-318 | — |
| 14 | 185-205 | −5.4 (c = 0.986 MeOH) |
| 15 | 196-197 | −51.3 (c = 1.03 MeOH) |
| 16 | 214-215 | +48.2 (c = 0.618 MeOH) |
| 17 | 264-268° C. | +61.1 (c = 0.32 MeOH) |
| 18 | 265-268 | −58.9 (c = 0.3 MeOH) |
| 19 | 207-208 | — |
| 20 | 214-215 | — |
| 21 | 210-211 | — |
| 22 | 215-217 | — |
| 23 | 210-212 | — |
| 24 | 336-339 | — |
| 25 | 271-273 | — |
| 26 | 290-291 | — |
| 27 | 317-318 | — |
| 28 | 314-315 | — |
| 29 | 315-316 | — |
| 30 | 215-230 | — |
| 31 | 210-220 | — |
| 32 | 328-330 | — |
| 33 | 275-280 | — |
| 34 | 338-344 | — |
| 35 | 295-300 | +55.2 (c = 0.3 MeOH) |
| 36 | 287-291 | — |
| 37 | >300 | — |
| 38 | 232-234 | — |
| 39 | 289-291 | — |
| 40 | 124-126 | — |
| 41 | 154-156 | — |
| 42 | 254-256 | — |
| 43 | 280-282 | — |
| 44 | 162-164 | +87.4 (c = 0.32; MeOH) |
| 45 | 275-277 | +43.8 (c = 0.32; MeOH) |
| 46 | 191-193 | +42.4 (c = 0.32; MeOH) |

TABLE 2-continued

| No. | m.p. (° C.) | $[\alpha]_D^{25}$ (°) |
|---|---|---|
| 47 | 234-236 | +53.2 (c = 0.30; MeOH) |
| 48 | 297-299 | +21.3 (c = 0.31; MeOH) |
| 49 | 284-286 | +68.6 (c = 0.32; MeOH) |
| 50 | 244-246 | +41.1 (c = 0.30; MeOH) |
| 51 | 194-196 | +73.9 (c = 0.29; MeOH) |
| 52 | 105-108 | +26.7 (c = 0.30; MeOH) |
| 53 | 169-171 | +82.3 (c = 0.30; MeOH) |
| 54 | 298-300 | +46.6 (c = 0.31; MeOH) |
| 55 | 213-215 | +75.9 (c = 0.30; MeOH) |
| 56 | 331-333 | +67.9 (c = 0.31; MeOH) |
| 57 | 295-297 | +79.4 (c = 0.30; MeOH) |
| 58 | 244-246 | +16.1 (c = 0.30; MeOH) |
| 59 | 282-284 | +26.4 (c = 0.31; MeOH) |
| 60 | 235-237 | +116.6 (c = 0.29; MeOH) |
| 61 | 278-280 | +14.2 (c = 0.30; MeOH) |
| 62 | 264-266 | +40.5 (c = 0.30; MeOH) |
| 63 | 128-130 | +61.9 (c = 0.32; MeOH) |
| 64 | 185-187 | +81.9 (c = 0.30; MeOH) |
| 65 | 329-331 | +45.9 (c = 0.29; MeOH) |
| 66 | 242-244 | +8.4 (c = 0.31; MeOH) |
| 67 | 284-286 | — |
| 68 |  | — |
| 69 | 291-293 | — |

The compounds of the invention were subjected to a series of pharmacological trials which demonstrated their importance as substances with therapeutic activity.

Study of the Transport of Glycine in SK-N-MC Cells Expressing the Native Human Transporter Glyt1.

The capture of [$^{14}$C]glycine is studied in SK-N-MC cells (human neuroepithelial cells) expressing the native human transporter glyt1 by measuring the radioactivity incorporated in the presence or in the absence of the test compound. The cells are cultured in a monolayer for 48 h in plates pretreated with fibronectin at 0.02%. On the day of the experiment, the culture medium is removed and the cells are washed with a Krebs-HEPES ([4-(2-hydroxyethyl)piperazine]1-ethanesulfonic acid) buffer at pH 7.4. After a preincubation of 10 min at 37° C. in the presence either of buffer (control batch), or of test compound at various concentrations, or of 10 mM glycine (determination of the nonspecific capture), 10 μM [$^{14}$C]glycine (specific activity 112 mCi/mmol) are then added. The incubation is continued for 10 min at 37° C., and the reaction is stopped by 2 washes with a Krebs-HEPES buffer at pH 7.4. The radioactivity incorporated by the cells is then estimated after adding 100 μl of liquid scintillant and stirring for 1 h. The counting is performed on a Microbeta Tri-lux™ counter. The efficacy of the compound is determined by the $IC_{50}$, the concentration of the compound which reduces by 50% the specific capture of glycine, defined by the difference in radioactivity incorporated by the control batch and the batch which received the glycine at 10 mM.

The most active compounds of the invention, in this test, have an $IC_{50}$ of the order of 0.001 to 10 μM.

The individual results for some compounds are as follows ($IC_{50}$ in μM):

| | |
|---|---|
| Compound No. 3 | 0.017 |
| Compound No. 4 | 0.004 |
| Compound No. 14 | 0.07 |
| Compound No. 17 | 0.001 |
| Compound No. 26 | 0.07 |

Ex Vivo Study of the Inhibitory Activity of a Compound on the Capture of [$^{14}$C]Glycine in Mouse Cortical Homogenate Increasing doses of the compound to be studied are administered by the oral route (preparation by trituration of the test molecule in a mortar in a solution of Tween/Methocel™ at 0.5% in distilled water) or by the intraperitoneal route (dissolution of the test molecule in physiological saline or preparation by trituration in a mortar in a solution of Tween/Methocel™ at 0.5% in water, according to the solubility of the molecule) to 20 to 25 g Iffa Crédo OF1 male mice on the day of the experiment. The control group is treated with the vehicle. The doses in mg/kg, the route of administration and the treatment time are determined according to the molecule to be studied.

After the animals have been humanely killed by decapitation at a given time after the administration, the cortex of each animal is rapidly removed on ice, weighed and stored at 4° C. or frozen at −80° C. (in both cases, the samples are stored for a maximum of 1 day). Each sample is homogenized in a Krebs-HEPES buffer at pH 7.4 at a rate of 10 ml/g of tissue. 20 μl of each homogenate are incubated for 10 min at room temperature in the presence of 10 mM L-alanine and buffer. The nonspecific capture is determined by adding 10 mM glycine to the control group. The reaction is stopped by filtration under vacuum and the retained radioactivity is estimated by solid scintillation by counting on a Microbeta Tri-lux™ counter.

An inhibitor of the capture of [$^{14}$C]glycine will reduce the quantity of radioligand incorporated into each homogenate. The activity of the compound is evaluated by its $ED_{50}$, the dose which inhibits by 50% the capture of [$^{14}$C]glycine compared with the control group.

The most potent compounds of the invention, in this test, have an $ED_{50}$ of 0.1 to 5 mg/kg by the intraperitoneal route or by the oral route.

Study of the Transport of Glycine in Mouse Spinal Cord Homogenate

The capture of [$^{14}$C]glycine by the transporter glyt2 is studied in mouse spinal cord homogenate by measuring the radioactivity incorporated in the presence or in the absence of the compound to be studied.

After the animals have been humanely killed (Iffa Crédo OF1 male mice weighing 20 to 25 g on the day of the experiment), the spinal cord of each animal is rapidly removed, weighed and stored on ice. The samples are homogenized in a Krebs-HEPES ([4-(2-hydroxyethyl)piperazine]1-ethanesulfonic acid) buffer, pH 7.4, at a rate of 25 ml/g of tissue.

50 μl of homogenate are preincubated for 10 min at 25° C. in the presence of Krebs-HEPES buffer, pH 7.4 and of compound to be studied at various concentrations, or of 10 mM glycine in order to determine the nonspecific capture. The [$^{14}$C]glycine (specific activity=112 mCi/mmol) is then added for 10 min at 25° C. at the final concentration of 10 μM. The reaction is stopped by filtration under vacuum and the radioactivity is estimated by solid scintillation by counting on a Microbeta Tri-lux™ counter.

The efficacy of the compound is determined by the concentration $IC_{50}$ capable of reducing by 50% the specific capture of glycine, defined by the difference in radioactivity incorporated by the control batch and the batch which received the 10 mM glycine.

The most active compounds of the invention in this test have an $IC_{50}$ of the order of 0.02 to 10 μM.

The $IC_{50}$ of the compound No. 17 is 0.69 μM.

The results of the trials carried out on the compounds of the invention of general formula (I) show that they are inhibitors of the glycine transporters glyt1 which are predominantly present in the brain, and of the glycine transporters glyt2, which are predominantly present in the spinal cord.

The compounds according to the invention can therefore be used for the preparation of medicaments, in particular of medicaments inhibiting the glycine transporters glyt1 and/or glyt2.

Thus, according to another of its aspects, the subject of the invention is medicaments which comprise a compound of formula (I), or an additional salt thereof with a pharmaceutically acceptable acid, or a hydrate or a solvate of the compound of the formula (I).

The compounds of the invention may be used in particular for the treatment of behavioral disorders associated with dementia, psychoses, in particular schizophrenia (deficient form and productive form) and acute or chronic extrapyramidal symptoms induced by neuroleptics, for the treatment of various forms of anxiety, panic attacks, phobias, obsessive-compulsive disorders, for the treatment of various forms of depression, including psychotic depression, for the treatment of disorders due to alcohol abuse or to withdrawal from alcohol, sexual behavior disorders, food intake disorders, and for the treatment of migraine.

Moreover, the compounds of the invention may be used for the treatment of painful muscular contractures in rheumatology and in acute spinal pathology, for the treatment of spastic contractures of medullary or cerebral origin, for the symptomatic treatment of acute and subacute pain of mild to moderate intensity, for the treatment of intense and/or chronic pain, of neurogenic pain and rebellious algia, for the treatment of Parkinson's disease and of Parkinsonian symptoms of neurodegenerative origin or induced by neuroleptics, for the treatment of primary and secondary generalized epilepsy, partial epilepsy with a simple or complex symptomatology, mixed forms and other epileptic syndromes as a supplement to another antiepileptic treatment, or in monotherapy, for the treatment of sleep apnea, and for neuroprotection.

The subject of the present invention is also pharmaceutical compositions containing an effective dose of at least one compound according to the invention, in the form of a pharmaceutically acceptable base or salt or solvate, and in the form of a mixture, where appropriate, with one or more suitable excipients.

Said excipients are chosen according to the pharmaceutical dosage form and the desired mode of administration.

The pharmaceutical compositions according to the invention may thus be intended for oral, sublingual, subcutaneous, intramuscular, intravenous, topical, intratracheal, intranasal, transdermal, rectal or intraocular administration.

The unit forms for administration may be, for example, tablets, gelatin capsules, granules, powders, oral or injectable solutions or suspensions, patches or suppositories. For topical administration, it is possible to envisage ointments, lotions and collyria.

By way of example, a unit form for administration of a compound according to the invention in tablet form may comprise the following components:

| | |
|---|---|
| Compound according to the invention | 50.0 mg |
| Mannitol | 223.75 mg |
| Croscarmellose sodium | 6.0 mg |
| Corn starch | 15.0 mg |
| Hydroxypropylmethylcellulose | 2.25 mg |
| Magnesium stearate | 3.0 mg |

Said unit forms contain doses in order to allow a daily administration of 0.01 to 20 mg of active ingredient per kg of body weight, according to the galenic form.

There may be specific cases where higher or lower dosages are appropriate; such dosages do not depart from the scope of the invention. According to the usual practice, the dosage appropriate for each patient is determined by the doctor according to the mode of administration, the weight and the response of said patient.

The present invention, according to its other aspects, also relates to a method for treating the pathologies indicated above, which comprises the administration, to a patient, of an effective dose of a compound according to the invention, or one of its pharmaceutically acceptable salts or the hydrates or solvates.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A pharmaceutical composition comprising a compound of the formula (I) or a pharmaceutically acceptable salt, a stereoisomer, a hydrate or a solvate thereof in combination with at least one pharmaceutically acceptable excipient:

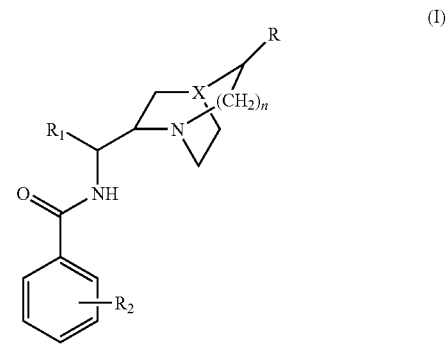

wherein
R represents a hydrogen atom;
n represents 1;
X represents a group of formula CH;
$R_1$ represents either a phenyl or naphthyl group optionally substituted with one or more substituents chosen from halogen atoms, linear or branched $(C_1\text{-}C_6)$alkyl, hydroxyl and $(C_1\text{-}C_6)$alkoxy groups, the trifluoromethyl group, or a cyclohexyl group, or a heteroaryl group chosen from thienyl, pyridinyl, oxazolyl, furanyl, thiazolyl, quinolinyl, and isoquinolinyl groups;
$R_2$ represents either a hydrogen atom, or one or more substituents chosen from halogen atoms, trifluoromethyl, $(C_1\text{-}C_6)$alkyl, $(C_1\text{-}C_6)$alkoxy, thienyl, phenyloxy, hydroxyl, mercapto,thio$(C_1\text{-}C_6)$alkyl and cyano group or a group of formula —$NR_4R_5$, $SO_2NR_4R_5$, —$SO_2$—$(C_1\text{-}C_6)$ alkyl,—$SO_2$-phenyl, —$CONR_4R_5$, —$COOR_7$, —CO—$(C_1\text{-}C_6)$alkyl, —CO-phenyl, —$NHCOR_8$, —$NHSO_2$—$(C_1\text{-}C_6)$-alkyl, —$NHSO_2$-phenyl and —$NHSO_2NR_4R_5$ or a group of formula —$OCF_2O$— attached at the 2- and 3-positions of the phenyl group; the groups $(C_1\text{-}C_6)$alkyl, —SO—$_2$—$(C_1\text{-}C_6)$alkoxy, —CO—$(C_1\text{-}C_6)$alkyl and —$NHSO_2$—$(C_1\text{-}C_6)$ alkyl being optionally substituted with one or more groups $R_3$;

the groups phenyl, —SO$_2$-phenyl, —CO-phenyl and —NHSO$_2$-phenyl being optionally substituted with a group R$_6$;

R$_3$ represents a halogen atom, or a phenyl, (C$_1$-C$_6$)alkoxy or —NR$_4$R$_5$ group;

R$_4$ and R$_5$ represent, independently of each other, a hydrogen atom or a (C$_1$-C$_6$)alkyl group or R$_4$ and R$_5$ form with the nitrogen atom bearing them a pyrrolidine ring, a piperidine ring or a morpholine ring;

R$_6$ represents a hydrogen atom, a halogen atom, a trifluoromethyl group, a cyano group, a hydroxyl group, a mercapto group, a (C$_1$-C$_6$)alkyl or (C$_1$-C$_6$)alkoxy group;

R$_7$ represents a hydrogen atom or a (C$_1$-C$_6$)alkyl group optionally substituted with one or more groups R$_3$, or a phenyl group optionally substituted with a group R$_6$;

R$_8$ represents a (C$_1$-C$_6$)alkyl group optionally substituted with one or more groups R$_3$, or a (C$_1$-C$_6$)alkoxy group, or a phenyl group optionally substituted with a group R$_6$; and said compound in the form of a free base or an addition salt with an acid, stereoisomer thereof.

2. The composition according to claim 1, wherein said compound is in the threo configuration.

3. The composition according to claim 1, wherein R$_1$ represents an optionally substituted phenyl group.

4. The composition according to claim 2, wherein R$_1$ represents an optionally substituted phenyl group.

5. The composition according to claim 1, wherein said compound is selected from the group consisting of:
  threo-2-chloro-N-[(1-azabicyclo[2.2.2]oct-2-yl)phenylmethyl]-3-trifluoromethylbenzamide hydrochloride 1:1;
  threo-2,6-dichloro-N-[(1-azabicyclo[2.2.2]oct-2-yl)phenylmethyl]-3-trifluoromethylbenzamide hydrochloride 1:1;
  2,6-dichloro-N-[(1S)-[(2S)(1-azabicyclo[2.2.2]oct-2-yl)phenylmethyl]-3-(trifluoromethyl) benzamide hydrochloride 1:1;
  threo-N-[1-Azabicyclo[2.2.2]oct-2-yl(4-fluorophenyl)methyl]-2,6-dichloro-3-(trifluoromethyl)benzamide hydrochloride 1:1; and
  said compound in the form of a free base or an addition salt with an acid thereof.

6. A pharmaceutical composition comprising 2-chloro-N—(8α,9S)cinchonan-9-yl)-3-trifluoromethylbenzamide hydrochloride 2:1 or a pharmaceutically acceptable salt thereof in combination with at least one pharmaceutically acceptable excipient.

* * * * *